(12) United States Patent
Meens et al.

(10) Patent No.: US 8,257,418 B2
(45) Date of Patent: Sep. 4, 2012

(54) BALLOON CATHETER WITH STENT AND METHOD FOR MANUFACTURING IT

(75) Inventors: Hendrik Jozef Maria Meens, Weert (NL); Derk Trip, Mierlo (NL)

(73) Assignee: C.R. Bard, Inc., Murray Hill, NJ (US)

( * ) Notice: Subject to any disclaimer, the term of this patent is extended or adjusted under 35 U.S.C. 154(b) by 1708 days.

(21) Appl. No.: 11/555,466

(22) Filed: Nov. 1, 2006

(65) Prior Publication Data

US 2007/0112408 A1    May 17, 2007

Related U.S. Application Data

(62) Division of application No. 10/140,479, filed on May 7, 2002, now abandoned.

(30) Foreign Application Priority Data

May 8, 2001 (NL) ....................................... 1018018
Sep. 4, 2001 (NL) ....................................... 1018881

(51) Int. Cl.
*A61M 29/02* (2006.01)
*A61F 2/82* (2006.01)

(52) U.S. Cl. .................. 623/1.11; 606/194; 604/103.08; 264/632; 425/394

(58) Field of Classification Search .................. 606/108, 606/194, 200; 623/1.11–1.54; 604/96.01, 604/103.06–103.09; 425/14, 303, 336, 369, 396, 394; 264/632

See application file for complete search history.

(56) References Cited

U.S. PATENT DOCUMENTS

| | | | | |
|---|---|---|---|---|
| 4,969,458 A * | 11/1990 | Wiktor | .................. | 623/1.11 |
| 5,066,298 A * | 11/1991 | Hess | .................. | 606/194 |
| 5,295,959 A * | 3/1994 | Gurbel et al. | .................. | 604/103.13 |
| 5,308,356 A * | 5/1994 | Blackshear et al. | .................. | 606/194 |
| 5,545,132 A * | 8/1996 | Fagan et al. | .................. | 604/103.08 |
| 5,693,066 A * | 12/1997 | Rupp et al. | .................. | 623/1.11 |
| 5,817,126 A * | 10/1998 | Imran | .................. | 623/1.15 |
| 5,913,871 A * | 6/1999 | Werneth et al. | .................. | 623/1.11 |
| 5,954,740 A * | 9/1999 | Ravenscroft et al. | .................. | 606/194 |
| 5,976,181 A * | 11/1999 | Whelan et al. | .................. | 623/1.12 |
| 6,289,568 B1 * | 9/2001 | Miller et al. | .................. | 29/423 |
| 6,942,681 B2 * | 9/2005 | Johnson | .................. | 606/194 |

* cited by examiner

*Primary Examiner* — Kathleen Sonnett
(74) *Attorney, Agent, or Firm* — King & Schickli, PLLC

(57) ABSTRACT

A balloon catheter includes a catheter tube, an inflatable balloon, the ends of which are attached to the catheter tube, and a stent attached around the balloon. The stent extends at least partly along the length of the balloon. In an uninflated state, at least the outside surface of the balloon not covered by the stent is provided with a relief structure which is substantially disappeared in an inflated state of the balloon. A related method involves manufacturing a balloon catheter.

12 Claims, 1 Drawing Sheet

# BALLOON CATHETER WITH STENT AND METHOD FOR MANUFACTURING IT

This application is a divisional of prior application Ser. No. 10/140,479, filed on May 7, 2002, now abandoned, the entire disclosure of which is incorporated by reference herein.

TECHNICAL FIELD

The present invention relates to a balloon catheter comprising a catheter tube, an inflatable balloon which at its ends is attached to the catheter tube and a stent attached around the balloon, wherein the stent extends at least in part along the length of the balloon. The invention further relates to a method of manufacturing a balloon catheter.

BACKGROUND INFORMATION

Balloon catheters of this type are generally known and are used for dilating vessels and lumina and for placing the stent in the dilated vessel or lumen. In order to pass the balloon catheter easily and safely through the vessels and lumina and to position it at the required place for dilatation, it is important that the balloon catheter has a small profile (outer diameter) and is sufficiently flexible.

The object of the invention is therefore to provide an improved balloon catheter.

BRIEF SUMMARY OF THE INVENTION

The balloon catheter according to the inventions characterized in that, in an uninflated state, at least the outside surface of the balloon that is not covered by the stent is provided with a relief structure which in an inflated state of the balloon is substantially disappeared.

Tests have shown that with a relief structure on the outside surface of the balloon a catheter is obtained that is more flexible than a standard balloon catheter. The balloon catheter according to the invention can therefore be passed more easily and more safely through vessels and lumina to the point of dilatation. Because of its flexibility, the catheter will be able to adapt better to a bend in a vessel or a lumen, thus reducing the risk of damage to the vessel or lumen.

The required relief structure may have different embodiments, but preferably comprises at least one groove that extends at least transversely in the longitudinal direction of the balloon in order to give the catheter the required flexibility in a direction transverse to the longitudinal direction thereof.

The groove preferably extends at a predetermined angle with respect to the longitudinal direction of the balloon. According to a preferred embodiment, the groove extends helically from one end to the other end of the balloon, over the outside surface thereof.

According to another embodiment, the relief structure comprises two or more grooves that extend helically from one end to the other end of the balloon, crossing each other. Flexible balloon catheter is obtained which also has a relatively low profile.

The invention also relates to a method for producing a balloon catheter comprising attaching the ends of an inflatable balloon to a catheter tube and placing a stent around the balloon, whereby according to the invention at least the outside surface of the balloon not covered by the stent is provided with a relief structure.

According to a first embodiment, the outside surface of the balloon is first provided with the relief structure and then the stent is attached around the balloon. An additional advantage of this embodiment is that a better fixing of the stent to the balloon is achieved. The improvement in fixing is due to the relief that makes the usual smooth surface of the balloon "rough". The stent adheres better to this rough surface.

According to a second embodiment, the stent is first attached around the balloon and then the outside surface is provided with the relief structure. A more flexible stent fixing system is obtained because at least the balloon material near the stent, both distally and proximally, is provided with a profile. Also, the stent placing system has obtained a smaller profile compared with known stent placing systems.

The relief structure is preferably produced on the application of heat to the surface of the balloon in order to deform the elastic material of the balloon.

The relief structure is also preferably produced on the surface of the balloon by applying a high pressure to the inside of the balloon.

According to a very inexpensive method, the relief structure is produced on the surface of the balloon by winding a wire around the balloon in the form of a helix.

According to another simple method, the relief structure is produced on the surface of the balloon by taking up the balloon in a counter-pressure body that has the relief structure.

BRIEF DESCRIPTION OF THE DRAWINGS

The invention is explained in more detail on the basis of the drawings attached. The drawings show.

DETAILED DESCRIPTION OF THE INVENTION

Figure 1A:
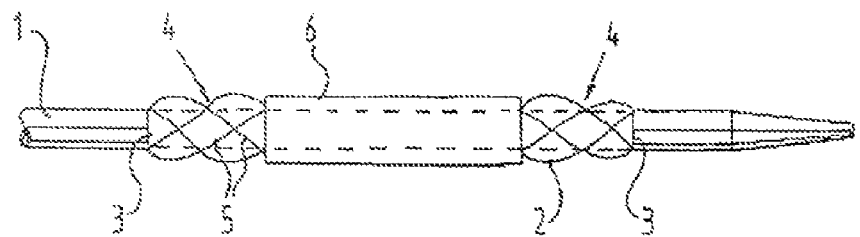
FIG. 1A is a side view of a form of a balloon catheter in an uninflated state.
Figure 1B:
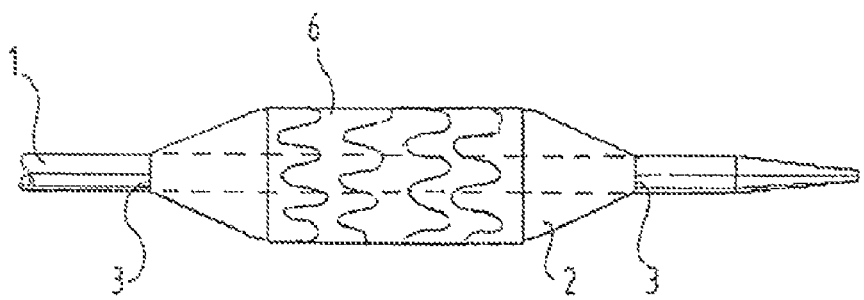
FIG. 1B is a side view of the catheter in FIG. 1A in an inflated state.

A balloon catheter according to the invention comprises a catheter tube 1, an inflatable balloon 2, which at its ends 3 is attached to the catheter tube 1, and a stent 6 attached around the balloon 2. The stent 6 extends partly along the length of the balloon 2 such that with the catheter, both distally and proximally next to the stent 6, balloon material lies freely. In an uninflated state (FIG. 1A), the outside surface of the balloon 2 has a relief structure 4 that in the inflated state has virtually or completely disappeared (FIG. 1B). The relief structure 4 gives the distal end of the catheter its required flexibility.

In the embodiments shown, the relief structure 4 consists of two grooves 5, which extend helically from one end 3 to the other end 3 of the balloon 2 and cross each other. The uninflated balloon 2 has thereby obtained a padded relief surface. It is also possible to provide a relief structure with a single helically shaped groove 5 whereby the uninflated balloon 2 displays a relief surface in the form of a helix. Other relief structures are of course possible, provided that the relief structure on the catheter creates the necessary flexibility in a direction transverse to the longitudinal direction of the balloon.

One way of obtaining the relief structure as shown in the drawings is by winding a wire helically around the balloon 2. This wire may, for example, be nylon wire or wire made of a different material that contracts somewhat on heating. After the wire has been wound around the balloon, a sleeve is pulled over the balloon. Subsequently, with the application of raised pressure to the inside of the balloon, the balloon is heated in such a way that in an uninflated state the balloon obtains a relief structure that on dilating of the balloon at the dilation site in the vessel or lumen will virtually or completely disappear. The sleeve is then removed and the balloon catheter can be inserted into a vessel or lumen.

Figure 2A:
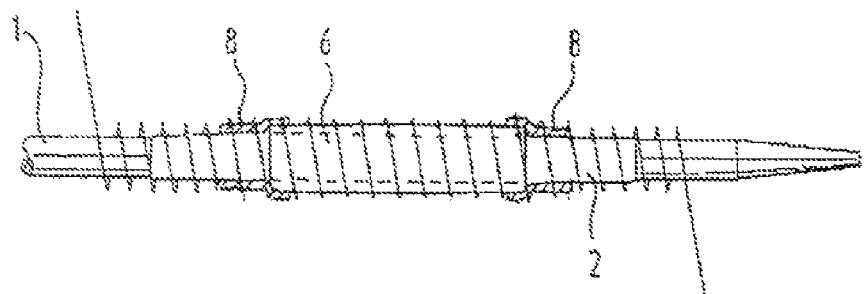
FIG. 2A is a side view of a second embodiment of a balloon catheter during the execution of the method according to the invention.
Figure 2B:
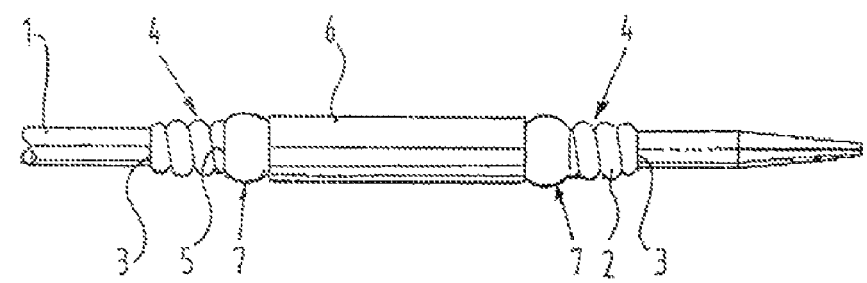
FIG. 2B is a side view of the final product of FIG. 2A.

The method according to the invention can be carried out in two ways. In the first way, the profile is first applied to the balloon by winding this around with wire and heating it under internal pressure, and then the stent is placed on the balloon. This results in improved flexibility and maneuverability of the distal part of the catheter. Better fixing of the stent on the "rough", profiled surface of the balloon is also achieved. In the second way, a stent is first placed on the balloon and then the complete distal part of the catheter, namely the balloon including the stent that has been placed in position, is wound around with wire, preferably nylon wire. Then the whole assembly is heated at a certain internal pressure. Winding produces a helical profile in the balloon material next to the stent. At the same time the diameter of the catheter with the stent is reduced because the nylon wire shrinks on heating. In a variation of this last method, first filler material 8 is placed next to the stent, over which wire is then also wound (see FIG. 2A). In the end this results in a small increase 7 in the balloon material next to the stent 6 (see FIG. 2B), into which the ends of the stent 6 can be pressed. As a result the ends of the stent 6 are better protected if the stent placing system is passed in a curved trajectory.

Instead of winding the wire, the balloon may be placed in a mould, which is provided with the relief pattern required, in order for it to obtain, under raised pressure and temperature, the relief structure required.

Before the balloon is provided with its relief structure, preferably it is folded in the usual way in order to reduce its profile. By applying the relief structure, the profile will be reduced as an additional, advantageous effect.

Note that, although it is not shown in the drawings, it is possible to provide the outside surface of the balloon with various helical grooves that cross each other. In addition to helical grooves, grooves of other shapes are also possible.

The balloon catheter may be used not only in cardiological but also radiological interventions.

What is claimed is:

1. Method for producing a balloon catheter for use in combination with a stent, the method comprising:
    folding a balloon in an uninflated state in a manner which reduces a profile of the balloon;
    forming at least one helical groove in an outside surface of the balloon including by winding a wire about at least a portion of the outside surface of the folded balloon in a direction having a component transverse to a longitudinal axis of the balloon wherein the at least one helical groove is substantially disappeared when the balloon is in an inflated state.

2. Method according to claim 1, wherein the forming step further comprises:
    raising an internal pressure of the balloon to a selected pressure;
    heating the resulting balloon structure; and
    removing the wire from the balloon wherein the at least one groove has been formed in the outside surface of the balloon.

3. Method according to claim 2, further comprising positioning the stent over the balloon after heating the balloon structure.

4. Method according to claim 1, wherein the wire is made of a material which contracts when heated.

5. Method according to claim 4, wherein the material is nylon.

6. Method according to claim 1, wherein the forming step comprises forming the groove extending from one end to the other end of the balloon.

7. Method for producing a balloon catheter for use in combination with a stent, the method comprising:
    folding a balloon in an uninflated state in a manner which reduces a profile of the balloon;
    forming at least one groove in an outside surface of the balloon from one end to the other end of the balloon, including by winding a wire about at least a portion of the outside surface of the folded balloon in a direction having a component transverse to a longitudinal axis of the balloon wherein the at least one groove is substantially disappeared when the balloon is in an inflated state.

8. Method according to claim 7, wherein the forming step further comprises:
    raising an internal pressure of the balloon to a selected pressure;
    heating the resulting balloon structure; and
    removing the wire from the balloon wherein the at least one groove has been formed in the outside surface of the balloon.

9. Method according to claim 8, further comprising positioning the stent over the balloon after heating the balloon structure.

10. Method according to claim 7, wherein the wire is made of a material which contracts when heated.

11. Method according to claim 10, wherein the material is nylon.

12. Method according to claim 7, wherein the forming step comprises forming a helical groove in the outside surface of the balloon.

* * * * *